(12) United States Patent
Patel et al.

(10) Patent No.: US 8,710,226 B2
(45) Date of Patent: Apr. 29, 2014

(54) PROCESS FOR THE PREPARATION OF MORPHINANE ANALOGUES

(71) Applicant: Sun Pharmaceutical Industries Ltd., Mumbai (IN)

(72) Inventors: Nileshkumar Sureshbhai Patel, Baroda (IN); Srinivasu Kilaru, Baroda (IN); Rajamannar Thennati, Baroda (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

(21) Appl. No.: 14/013,873

(22) Filed: Aug. 29, 2013

(65) Prior Publication Data

US 2014/0031550 A1    Jan. 30, 2014

Related U.S. Application Data

(62) Division of application No. 12/935,831, filed as application No. PCT/IN2009/000203 on Mar. 23, 2009, now Pat. No. 8,546,572.

(30) Foreign Application Priority Data

Mar. 31, 2008  (IN) ............................ 722/MUM/2008

(51) Int. Cl.
*C07D 489/12*   (2006.01)
*C07D 489/02*   (2006.01)

(52) U.S. Cl.
USPC ............................................ 546/39; 546/44

(58) Field of Classification Search
USPC ...................................................... 546/39, 44
See application file for complete search history.

(56) References Cited

U.S. PATENT DOCUMENTS 5,849,915 A * 12/1998 Kim et al. ...................... 546/39
2007/0167474 A1    7/2007 Schmidhammer

* cited by examiner

*Primary Examiner* — Charanjit Aulakh
(74) *Attorney, Agent, or Firm* — Sughrue Mion, PLLC

(57) ABSTRACT

The present invention relates to an improved process for preparing morphinane analogues of formula 1

Formula 1 wherein the substituents $R_1$, $R_2$, $R_{2a}$, $R_3$, $R_4$, $R_5$ and Y have the meanings as defined in the specifications.

12 Claims, No Drawings

PROCESS FOR THE PREPARATION OF MORPHINANE ANALOGUES

CROSS REFERENCE TO RELATED APPLICATIONS

This is a divisional application of U.S. application Ser. No. 12/935,831 filed on Dec. 16, 2010, which is a National Stage of International Application No. PCT/IN2009/000203, filed on Mar. 23, 2009, which claims priority from Indian Patent Application No. 722/MUM/2008, filed on Mar. 31, 2008, the contents of all of which are incorporated herein by reference in their entirety.

FIELD OF INVENTION

This present invention relates to a novel, improved process for the synthesis of certain morphinane analogues.

BACKGROUND OF THE INVENTION

The present invention relates to a novel process for preparation of morphinane analogues i.e compounds of formula I. The morphinanes may be characterised by a common chemical structure that of a cyclic tertiary amine represented by following structure:

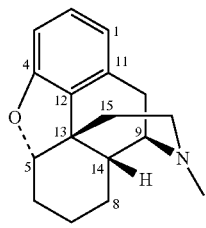 [SMILES: CN1CC[C@]23c4c5cccc4O[C@H]2CCC[C@H]3[C@H]1C5]

These analogues exert their effect at the opioid receptors in the central nervous system and other tissues and are useful as pharmaceutical substances for treatment of pain, drug abuse and various other disorders. Because of the high potency and diverse uses of the morphinane derivatives in therapy for human as well as for veterinary use, there is an increasing demand for medicinal morphinanes. Some of the morphinane analogues known in the art are as follows:

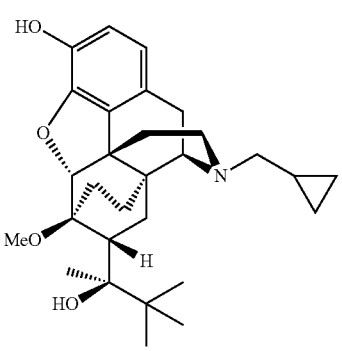

Buprenorphine

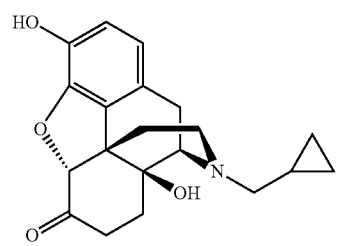

Naltrexone

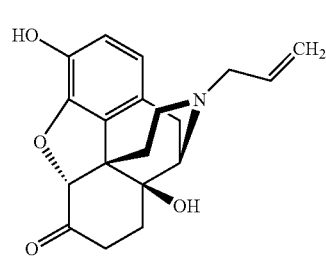

Naloxone

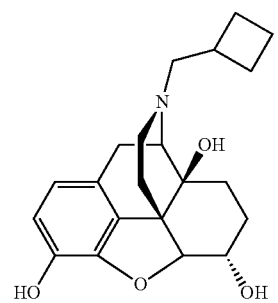

Nalbuphine

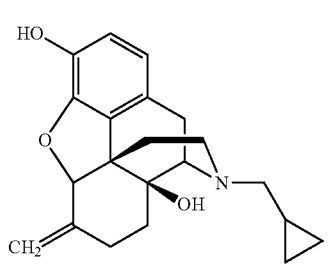

Nalmefene

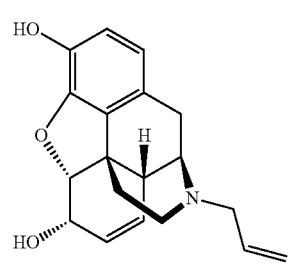

Nalorphine

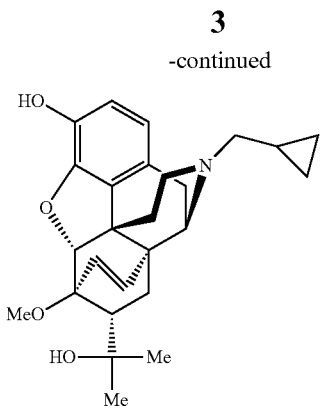
Cyprenorphine

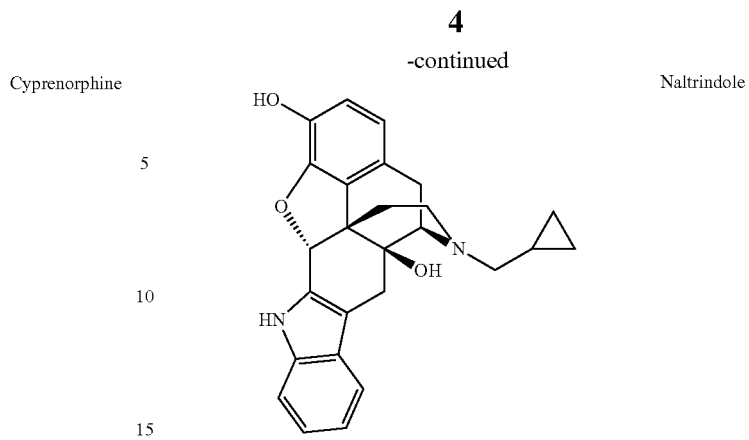
Naltrindole

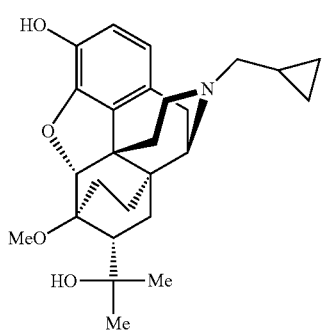
Diprenorphine

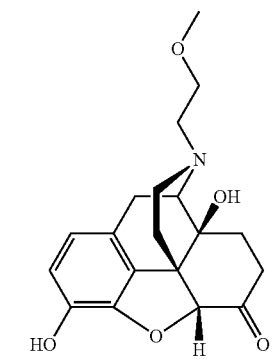
Semorphone

The prior known processes for preparation of the morphinane analogues generally begin with thebaine or its O-demethylated derivative, oripavine. Thebaine occurs naturally in plant sources from which it is extracted and purified by an expensive and laborious procedure. Thebaine-producing plants require special agronomical and environment conditions which can further increase the final cost of thebaine extracted therefrom. Consequently, there is a need for a process of preparation of morphinane derivatives which gives high yields of quality products and which uses safer solvents and reagents.

The process for the preparation of morphinane derivatives comprises mainly of two steps starting from thebaine or oripavine namely the. N-demethylation and N-alkylation. The following patent references generalize the state of art for the N-dealkylation of thebaine or oripavine.

U.S. Pat. No. 3,433,791 (as referred to as '791) discloses endoethano northebaine and nororipavine derivatives, including, N-cyclopropylmethyl-6,14-endoethano-7-(2-hydroxy-2-methyl-2-tertbutyl)-tetrahydronororipavine commonly known as Buprenorphine. The '791 patent describes N-demethylation of endoethano thebaine and oripavine derivatives in a two step process, first step involving formation of N-cyano derivative using cyanogen bromide followed by hydrolysis of the N-cyano derivative to yield the N-demethylated product. The process gives a lower yield (~70%) of the N-demethylated product and further requires the use of cyanogen bromide, which is toxic and requires great precautions for use in large scale. The following scheme 1 outlines the process of preparation of buprenorphine as disclosed in the '791 patent.

Scheme 1

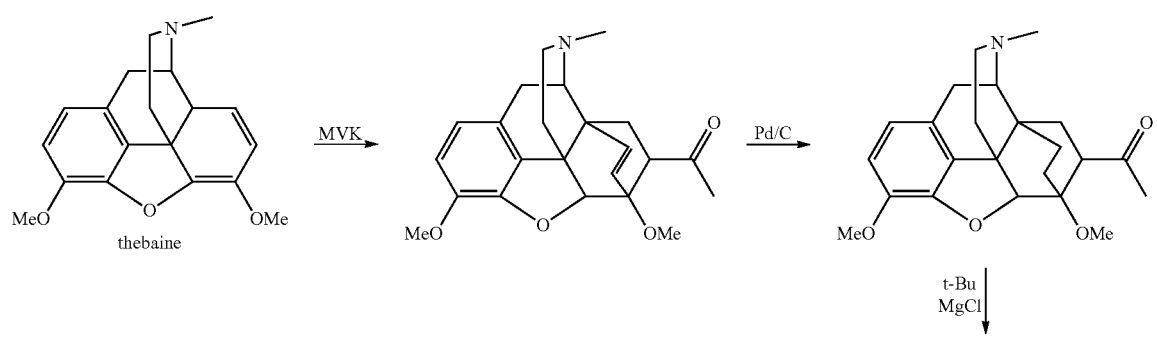

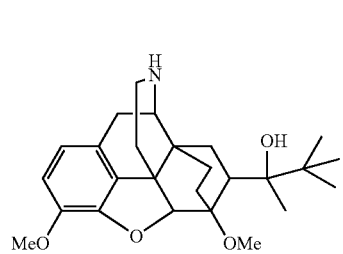 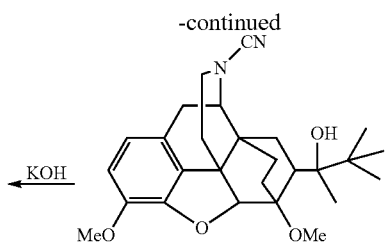 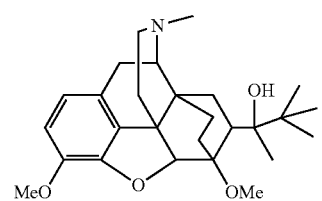

-continued

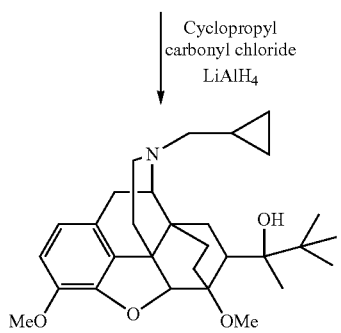

Buprenorphine

Canadian Patent No. 2597350, discloses preparation of noroxymorphone derivatives like naltrexone and naloxone. It discloses N-demethylation of noroxymorphone using ethyl chloroformate in presence of basic conditions to prepare noroxymorphone carbamate which is hydrolyzed to form the N-demethylated derivative. More specifically, it describes the N-demethylation of diacetyloxymorphone to form diacetyloxymorphone carbamate, which is then hydrogenated to yield noroxymorphone i.e. the N-demethylated derivative. The yield of the N-demethylated product is ~65% based on the starting material used. Further, European Patent No. 164290 discloses a similar process for preparation of 14-hydroxymorphinanes with lower yields. It was found by us that with the use of ethylchloroformate for N-demethylation of compounds of formula I of the present invention, the reaction did not go to completion and the yields obtained were lower.

Also, U.S. Pat. No. 4,141,897 discloses use of vinyl chloroformate for N-demethylation of N-alkyl-14-hydroxymorphinans, however, the process suffers from disadvantages in that the yield obtained is 70-85%, the instability of the reagent leads to variable output and its delicate preparation requires high cost.

The process of present invention does not use toxic reagents like cyanogen bromide for N-demethylation, instead uses an $C_{1-4}$alkylchloroformate along with an alkali iodide and a heterogenous base, for the N-demethylation of thebaine or oripavine derivatives. The process gave higher yields, which is near the theoretically calculated value, of the N-demethylated derivative with good purity. The use of alkali iodide along with an $C_{1-4}$alkylchloroformate and a base, according to the present invention, has not been disclosed heretobefore for N-demethylation of the morphinane analogues.

Further, N-alkylation of the morphinane analogues is described in several references, for example, U.S. Pat. No. 3,332,950 (referred to as '950 hereinafter), which discloses 14-hydroxydihydronormorhinones, specifically, naltrexone and methods of preparing the same. The '950 patent discloses two methods for N-alkylation of morphinane derivatives disclosed therein. In one of the methods, N-alkylation is carried out in a two-step reaction. The first step involves use of cyclopropylcarbonyl chloride to obtain a carbonylalkyl substituted compound which was subjected to reduction using lithium aluminium hydride (LiAlH$_4$), in the second step to generate the N-alkylated compound. The method is disadvantageous in that it involves a two-step reaction for N-alkylation, uses highly reactive, pyrophoric metal hydride reagent like LiAlH$_4$ and affords yield of approximately 33% starting from noroxymorphone. In another method (Scheme 2) 14-hydroxydihydronormorphinone is treated with cyclopropylmethyl bromide in DMF to prepare naltrexone. The method employs high temperatures and prolonged reaction time (7 days) yet achieves only a 60% of theoretical yield.

Scheme 2

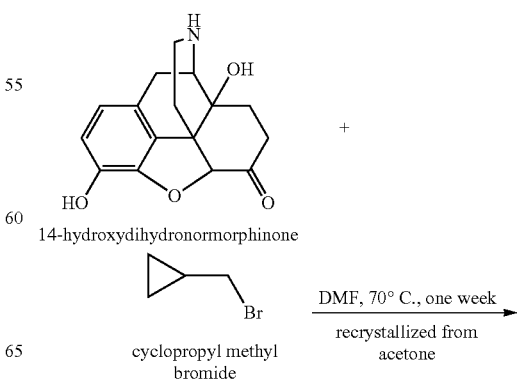

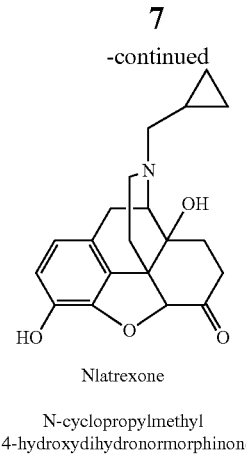

Nlatrexone

N-cyclopropylmethyl
14-hydroxydihydronormorphinone

British Patent No. 1119270 discloses 14-hydroxydihydronormorphine derivatives such as Nalbuphine. In one of the methods disclosed therein, cyclobutylmethyl bromide is employed for N-alkylation. A similar process for preparation of buprenorphine, Naloxone and Nalorphine has been disclosed in the '791 patent, British Patent No. 939287 and U.S. Pat. No. 2,364,833, respectively, wherein the corresponding alkylhalide has been used for N-alkylation of morphinane derivatives. We have found that when the N-alkylation reaction using corresponding alkyl or cycloalkylbromide is not a clean reaction, the reaction is slow, does not go to completion and leads to an impure product. It was surprisingly found by us that the use of the corresponding alkanol, a $C_{1-3}$alkyl sulfonylhalide and an alkali metal halide, in a single-step, for N-alkylation, hitherto not reported in literature for morphinane analogues, led the reaction to completion with corresponding increase in yield and quality of the product.

In addition to the N-demethylation and N-alkylation reactions, the process of preparation of a morphinane analogue, namely buprenorphine, starting from thebaine, comprises reactions for introducing endoethano bridge at the 6- & 14-position, addition of a tertiary butyl group to the carbonyl of 7-acetyl group via grignard reaction and O-demethylation reaction (See Scheme I above). The process as generically disclosed for the endoethano compounds in the '791 patent comprises reaction of thebaine with methyl vinyl ketone to form the 7-acetylendoetheno compound via a 4+2 reaction, hydrogenation of the carbon-carbon double bond of the endoetheno bridge using high hydrogen pressure, addition of a tertiary butyl group to the carbonyl of 7-acetyl group via a grignard reaction employing benzene or diethylether or a combination of these as a solvent and O-methylation reaction which is carried out at a temperature of >200° C. in presence of an alkali. Also U.S. Pat. No. 5,849,915 which discloses certain buprenorphine analogues, prepares endoetheno derivatives of morphinanes by reacting thebaine with methyl vinyl ketone in a molar ratio of about 1:1746.

The process as disclosed in the '791 and the '915 patent for preparation of buprenorphine or its precursors suffers from disadvantages, in that the process is low yielding, for example, in the '791 patent the yields of the product obtained at each step is in the range of 25-70% with the overall yield of only 4.5%. The prior art process for preparation of endoethano compounds as disclosed in the '915 patent uses a large excess of methylvinyl ketone which is not only expensive but also is lachrymatic in nature, which causes inconvenience in large scale synthesis. The hydrogenation step, as disclosed above, uses high hydrogen pressure ~58 psi furnishing yield of only ~60%. The grignard reaction employs a combination of benzene and diethylether as solvent, which not only gives a low yield on ~25%, but is also not advisable because of known carcinogenicity of benzene. Further, the O-demethylation reaction requires harsh environment i.e. high temperatures in presence of an alkali which may cause an irreversible damage to the phenolic moiety as observed in poor yield, obtained for this reaction.

The process of the present invention is advantageous in that it uses of methylvinylketone in a quantity which is only four times the molar quantity of thebaine, yet furnishes a high yield of ~90%. Further, the hydrogenation reaction is carried out at atmospheric pressure in 10% aqueous acetic acid, furnishing ~83.0% yield. The grignard reaction of the 7-acetylated derivative, according to the present invention, avoids the toxic solvents like benzene, and instead uses solvents like tetrahydrofuran or diethylether or mixtures thereof, which are relatively safer with a 3-fold improvement in yield of the product. Further, the process uses thiols for the O-demethylation reaction and requires use of less harsher conditions of temperature, leading to a further improvement in yield.

In summary, the state of art for synthesis of morphinane analogs uses reagents and solvents which are not eco-friendly. The synthesis of the analogues involves several steps with low yields at several stages. Further the use of hazardous solvents, high pressure and high temperature reactions, prolonged reactions, contribute to the cost of production, inconsistent quality and requirement of large excess of expensive and controlled starting materials like thebaine. Thus, even though, the prior art discloses several processes for the preparation of morphinane derivatives, they have largely been unsuccessful in providing a process with high yield with safer reagents and solvents. The present invention involves steps furnishing high yields, employs stoichiometric quantities of reagents and uses class-2 and class-3 solvents which are relatively innocuous. The process of the present invention utilizes moderate reaction conditions, has reduced reaction time and furnishes high quality of the end products, all of which contribute significantly towards making the process economical. Furthermore, the process uses stable reagents and produces reproducible results.

DESCRIPTION OF THE INVENTION

The present invention relates to novel process for preparation of compounds of formula 1 or salts thereof

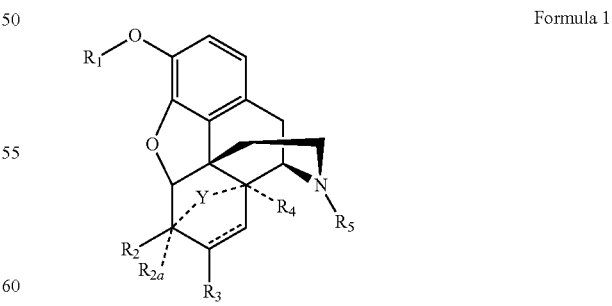

Formula 1 wherein,
$R_1$ is hydrogen;
$R_2$ and $R_{2a}$ are independently selected from hydrogen, hydroxy or methoxy;
or $R_2$ and $R_{2a}$ together represent =O or =CH$_2$;

$R_3$ is selected from hydrogen or a group of the formula A

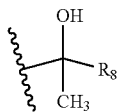

Formula A wherein $R_8$ is selected from methyl or t-butyl;
or $R_2$ and $R_3$ together may form, together with the carbon atoms to which they are attached a group of the formula B

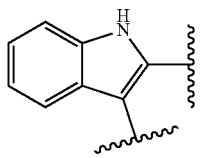

Formula B $R_4$, when present, is in beta conformation and is selected from hydrogen, hydroxy;
$R_5$ is selected from $C_{3-8}$ alkyl, alkenyl, alkynyl, cycloalkylalkyl, arylalkyl, alkoxyalkyl;
Y is ethano or etheno
the dotted lines ------ indicate an optional single bond;
with a proviso that when Y is present, $R_4$ and $R_{2a}$ are absent and when $R_2$ and $R_3$ together with the carbon atoms to which they are attached form a group of formula B, $R_{2a}$ is absent.
which comprises the steps of:
(a) reacting a compound of formula 2

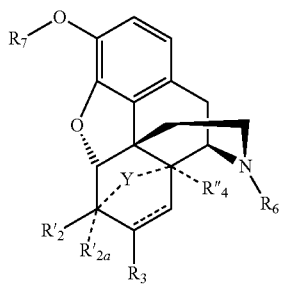

Formula 2 wherein,
$R'_2$ and $R'_{2a}$ are selected from hydrogen, methoxy or —O—R', wherein R' is an oxygen protecting group,
or $R'_2$ and $R'_{2a}$ together represent =O or =CH$_2$;
$R_6$ is methyl,
$R_7$ is methyl or an oxygen protected group,
$R''_4$ when present, is in beta conformation and is selected from hydrogen or an —O—R' wherein R' is an oxygen protecting group
$R_3$, Y and the dotted lines ----- have the meaning as defined above in formula 1;
with $C_{1-4}$alkylchloroformate, wherein the alkyl group is unsubstituted or substituted with one or more chloro or methyl groups; in presence of an alkali iodide and a base to obtain a compound of formula 3,

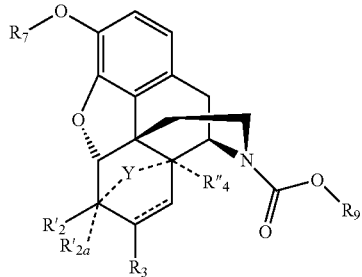

Formula 3 wherein $R_9$ is $C_{1-4}$alkyl wherein the alkyl group is unsubstituted or substituted with chloro or methyl groups;
$R'_2$, $R'_{2a}$, $R_3$, $R''_4$, $R_7$, Y and the dotted lines ----- have the meaning as defined above;
b) subjecting the compound of formula 3 to hydrolysis in presence of an acid or a base to obtain a compound of formula 4,

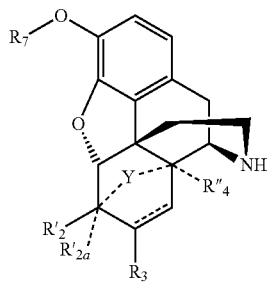

Formula 4

(c) reacting the compound of formula 4 with a compound of formula 5

$R_5$—OH    Formula 5 wherein, $R_5$ has the meaning as defined in formula 1, in presence of an $C_{1-3}$alkyl sulfonyl halide, LiBr and a base to obtain the compound of formula 6;

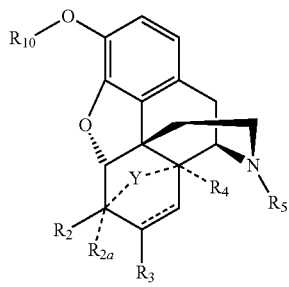

Formula 6 wherein $R_{10}$ is hydrogen or methyl;
d) converting the compounds of formula 6 to a compound of formula 1 or salts thereof.

DETAILED DESCRIPTION OF THE INVENTION

Step a, as disclosed above, is a method for preparation of carbamate derivatives of compounds of formula 2 and involves reaction of a compound of formula 2 with an $C_{1-4}$alkylchloroformate, wherein the alkyl group is linear or branched and is unsubstituted or substituted with one or more halogen, in presence of an alkali iodide and a base to obtain a compound of formula 3. A suitable $C_{1-4}$alkylchloroformate which may be used in the present invention may be, for example, methylchloroformate, ethylchloroformate, α-chloro ethylchloroformate, isobutylchloroformate and the like. Preferably the $C_{1-4}$alkylchloroformate is ethylchloroformate. Suitable alkali iodide for the reaction may be, for example, sodium iodide or potassium iodide, preferably, sodium iodide may be used. The base which may be used in the present process may be a heterogenous base selected from alkali or alkali earth metal hydroxides, carbonates or bicarbonates. A suitable alkali carbonate may be sodium carbonate, sodium carbonate, potassium carbonate or lithium carbonate. Preferably, the base used in lithium carbonate.

In a preferred embodiment, the $C_{1-4}$alkylchloroformate, the base and the alkali iodide compounds may be used in a molar ratio of about 1:3:5.

The reaction may be carried out in presence of an organic solvent. The organic solvent which may be used for the reaction may be selected from an inert solvent or a polar aprotic solvent. An inert solvent for the reaction may be an aromatic hydrocarbon solvent such as toluene, xylene etc. A polar aprotic solvent for the said reaction may be halogenated solvents chlorobenzene, ethylene dichloride, methylene dichloride and the like.

The compounds of formula 2, wherein one or more hydroxy groups are protected with suitable protecting groups, may be prepared from the corresponding hydroxy precursors. Such reactions for protecting oxygen radical, are well known in the art. The suitable oxygen protecting groups for the process of the present invention are, for example, acyl, benzyl, naphthylmethyl, t-butyl, silyl, preferably acyl, more preferably acetyl. The hydroxyl precursors of compounds of formula 2 may be first reacted with a suitable protecting group to obtain a compound of formula 2 with protected hydroxyl groups, which may then be subjected to subsequent reaction as disclosed herein in step a. The compound of formula 3 formed in step a may be subjected to step b without further purification.

Step b involves hydrolysis of the carbamate derivative formed in step a above to obtain the N-demethylated derivative. The step involves hydrolysis of compound of formula 3, to obtain a compound of formula 4. The hydrolysis reaction can be carried out using acidic or basic reagents generally known in the art such as hydrochloric acid, potassium hydroxide, sulfuric acid etc. Basic hydrolysis is carried out, preferably using potassium hydroxide in presence of polar solvents such as ethylene glycol or diethylene glycol, more preferably, diethylene glycol. For acidic hydrolysis, strongly acidic conditions are used, particularly, 5 to 10 N sulphuric acid. Preferably, mixture of sulfuric acid and acetic acid is used, such that the less degradation products are formed. The hydrolysis of the carbamate is accompanied by the removal of the oxygen protecting group.

Step c as disclosed above, involves N-alkylation of a compound of formula 4, using a compound of formula 5 in presence of $C_{1-3}$alkyl or aryl sulfonyl chloride, an alkali metal halide and a base. The $C_{1-3}$alkylsulfonyl chloride may be selected from methanesulfonyl chloride, ethanesulfonyl chloride or propane sulfonylchloride. Aryl sulfonyl halide may be selected from benzene sulfonylchloride, p-toluene-sulfonylchloride. More preferably the $C_{1-3}$alkyl or aryl sulfonylchloride is methane sulfonyl chloride. The alkali metal halide, may be selected from sodium bromide, potassium bromide, lithium bromide etc. Preferably, the alkali metal halide is lithium bromide. A suitable base for the reaction may be selected from organic base such as triethylamine, diisopropylamine, triethylamine being preferred. The reaction may be carried out in an organic polar aprotic solvents or mixtures thereof. The polar aprotic solvent may be selected from dimethylformamide (DMF), dimethylsulfoxide (DMSO), N-methylpyrrolidine (NMP), sulfolane, tetrahydrofuran etc. More preferably the solvent is dimethylformamide.

Step d involves converting the N-alkylated compounds of formula 6 to compounds of formula 1 or salts thereof. Depending on the final compound of formula-I sought to be prepared and the compound of formula 6 obtained, this step may involve reactions as cited hereinafter. According to one embodiment of process of the present invention, the compounds of formula 6, wherein $R_{10}$ is methyl, step d may involve O-demethylation to obtain a compound of formula 1. O-demethylation of the morphinane derivative may be carried out using an alkali metal alkoxide and an $C_{1-4}$alkyl or arylthiol in a suitable solvent. The alkali metal alkoxide may be selected from sodium alkoxides, such as sodium t-butoxide, sodium methoxide, sodium ethoxide; or potassium alkoxides such as potassium t-butoxide, potassium methoxide, potassium ethoxide, and the like. Preferably the alkali metal alkoxide is potassium t-butoxide The $C_{1-4}$alkyl thiols for the reaction may be, for example, propanethiol, methionine, butylthiol, t-butylthiol. The arylthiol may be selected from thiophenol, 1-naphthalenthiol, 2-naphthalenethiol etc. Preferably the aryl thiol is thiophenol. The reaction can be carried out in polar organic solvents like DMF, DMSO, NMP (1-methyl-2-pyrrolidinone), DMA (N,N-dimethylacetamide), DEF (N,N-diethylformamide), DEA (N,N-diethylacetamide), HMPA (hexamethyl phosphoramide), DMPU (1,3-dimethyl-3,4,5,6-tetrahydro-2(1H)-pyrimidinone) and DMEU (1,3-dimethyl-2-imidazolidinone). Preferably the reaction is carried out in DMSO or NMP. More preferably the reaction is carried out in DMSO. The reaction may be advantageously carried out at a temperature below 200° C., preferably at a temperature ranging from 100 to 150° C., more preferably at about 130° C. The O-alkylated morphinane derivatives can be optionally converted to salts thereof.

The compounds of formula 1, wherein $R_2$ and $R_3$ together with the carbon atom to which they are attached may form a group of the formula B, may be prepared from a compound of formula 6, by a process described in U.S. Pat. No. 4,816,586 (referred to as '586 hereinafter) which is incorporated herein as a reference.

The compounds of formula 1, wherein $R_2$ is hydroxy and $R_{2a}$ is hydrogen, may be prepared from compound of formula 6 wherein $R_2$ and $R_{2a}$ is oxo by subjecting such a compound of formula 6 using a suitable metal hydride reagent as disclosed in British patent No. 1119270 (referred to as '270), which is incorporated herein as a reference. Likewise, compounds of formula 1, wherein $R_2$ and $R_{2a}$ represent methylidene can be prepared from compound of formula 6 according to a process disclosed in British Patent No. 1411129 (referred to as '129 hereinafter), which is incorporated herein as a reference.

For compounds of formula 6, wherein $R_{10}$ is hydrogen, step d may involve converting the compounds of formula 6 to their salts.

The salts of compounds of formula 1 can be prepared according to the conventional process for preparation of salts. Since the compound of formula I possess a basic nitrogen group in its structure, it can form acid addition salts. The acid salts may be mineral acid salts (e.g. hydrochloride, hydrobromide, sulfate), organic acid salts (e.g. citrate succinate, maleate, fumarate, malate, tartarate, myristate, pamoate, etc.) and sulfonates (e.g. methanesulfonates, benzenesulfonates, toluensulfonates) and other salts which are customarily employed in pharmaceutical filed in connection with the nitrogen-containing compounds.

In a preferred embodiment, the present invention relates to process of preparing compound of formula 1, represented by compound of formula 1a

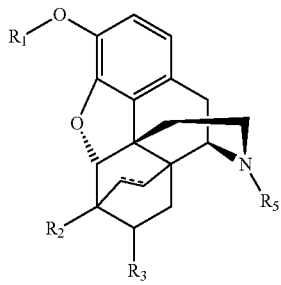

Formula 1a wherein,
$R_1$ is hydrogen;
$R_2$ is selected from hydroxy or methoxy;
$R_3$ is selected from hydrogen or a group of the formula A

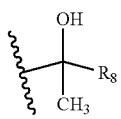

Formula A wherein $R_8$ is selected from methyl or t-butyl;
$R_5$ is selected from $C_{3-8}$ alkyl, alkenyl, alkynyl, cycloalkylalkyl, arylalkyl, alkoxyalkyl. the dotted lines ------ indicate an optional single bond;

In another preferred embodiment, the compound of formula 1 is represented by compound of formula 1b

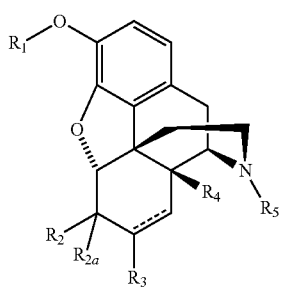

Formula 1b wherein,
$R_1$ and $R_3$ are hydrogen;
$R_2$ and $R_{2a}$ are independently selected from hydrogen, hydroxyl or methoxy;
or $R_2$ and $R_{2a}$ together represent =O or =CH$_2$;
or $R_2$ and $R_3$ together may form together with the carbon atoms to which they are attached a group of the formula B,

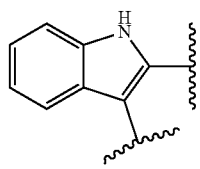

Formula B $R_4$ is selected from hydrogen, hydroxy;
$R_5$ is selected from $C_{3-8}$ alkyl, alkenyl, alkynyl, cycloalkylalkyl, arylalkyl, alkoxyalkyl; the dotted lines ----- indicate an optional single bond.

with a proviso that when $R_2$ and $R_{2a}$ together represent =O, $R_2$ and $R_3$ together with the carbon atoms to which they are attached, cannot form a group of formula B The compound of formula 2, used in step a above is known in the art. According to a preferred embodiment, the present invention relates to an improved process of preparation of a compound of formula 2, represented by compounds of formula 2a,

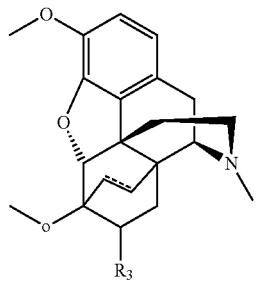

Formula 2a wherein $R_3$ is a group of the formula

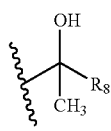

wherein $R_8$ is selected from methyl or t-butyl. The compounds of formula 2a may be prepared by a process as outlined in scheme 3 below.

Scheme 3

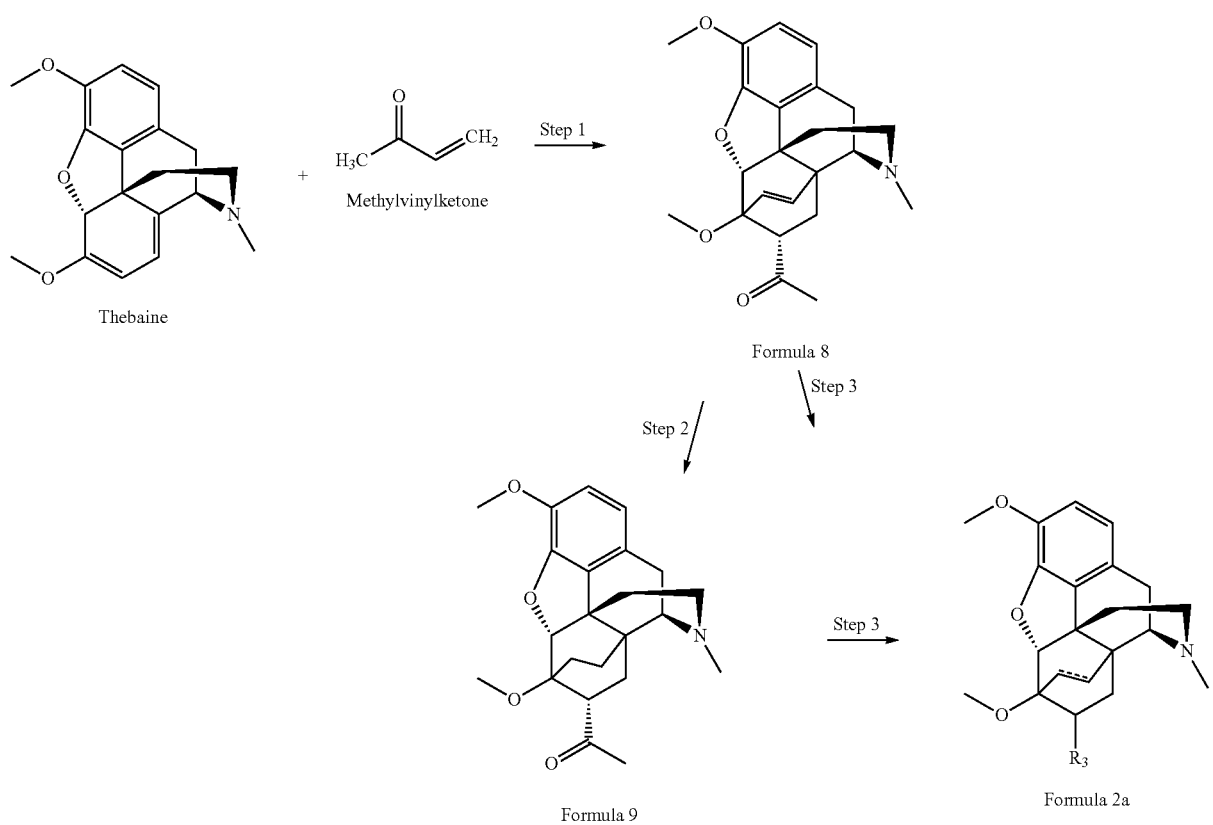

The process comprises of the following steps 1 to 3:

Step 1 involves reacting thebaine with methylvinyl ketone to obtain a compound of formula 8

The reaction is an example of Diels-Alder reaction which is generally well known in the art. In a preferred embodiment the reaction may be carried out using thebaine and methylvinylketone in a ratio of about 1:4. The reaction can be performed by refluxing the two reactants in a suitable solvent. The suitable solvent for the reaction may be selected from isopropyl alcohol, methanol, ethanol, toluene and mixtures thereof. Alternatively, the reaction may be advantageously carried out in absence of a solvent.

Step 2 of the process, may be optional and involves hydrogenation of the endoetheno compound obtained in step 1 above to obtain endoethano bridged compounds of formula 9. Step 2 is optional and is carried out only in compounds of formula 2a wherein the 6- and 14-position are linked by an endoethano bridge. Hydrogenation may be carried out using a catalytic hydrogenating process at atmospheric pressure to obtain a compound of formula 9, possessing a saturated endoethano bridge. A suitable metal catalyst may be used for the process. The metal catalyst may be, for example, Pd, Pt or Raney Nickel. The reaction may be carried out in presence of a polar organic solvent or mixtures thereof. The solvent may be selected from organic acids such as glacial acetic acid or formic acid or a mixture of these, alcohols preferably methanol, ethanol, isopropyl alcohol, n-butanol or a mixture of these. More preferably the reaction is carried out in glacial acetic acid. In a preferred embodiment, the hydrogenation can be carried out at atmospheric pressure.

Step 3 involves reacting the product of step 1 or step 2, i.e. the compound of formula 8 or 9 with a grignard reagent, $R_8MgX^-$, wherein $X^-$, represents a halide radical to obtain a compound of formula 2a above. The grignard reagent may be prepared by combining magnesium with the desired alkyl halide and iodine in a suitable organic solvent or mixtures thereof, under moisture free conditions, in an inert atmosphere. Such a process for preparation of grignard reagent is well known in the art. A solution of compound of formula 8 or 9 in a suitable solvent as mentioned herein below may be added to the thus prepared grignard reagent to obtain a compound of formula 2a.

The reaction may be carried out in presence of a suitable organic solvent or mixtures thereof. The suitable organic solvent may be selected from tetrahydrofuran, dioxane, diisopropyl ether, di-tertiary butyl ether or diethylether.

Surprisingly, it was found by us that the concentration of tetrahydrorfuran in diethylether determines the yield as well as the quality of the product obtained. It was observed that use of about 1-15% of tetrahydrofuran in ether improved the yield and the quality of the alkylated product. Accordingly, in one of the preferred embodiment, the grignard reaction is carried out in presence of diethylether containing about 1-15% of tetrahydrofuran, more preferably, the solvent is diethylether containing about 6-10% of THF.

The compounds of formula 2a thus formed may be subjected to a series of reactions involving N-demethylation to obtain the compounds of formula 4, N-alkylation to obtain a compound of formula 6, and/or O-demethylation as described in steps a to d above, in detail. Alternatively, the compounds of formula 2a may be subjected to O-demethylation first, by following a process similar to that described in step d for compounds of formula 6, wherein $R_{10}$ is methyl.

In a preferred embodiment, the compound of formula 2a is represented by compound of formula 2c.

Formula 2c

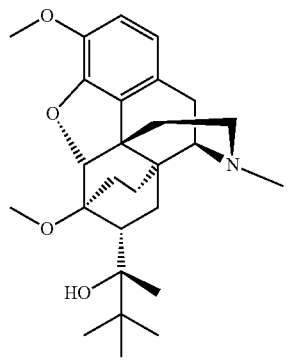

The compound of formula 2c can be prepared by a process as described for formula 2a above. The process comprises the steps of Step 1 reacting thebaine with methylvinyl ketone to form a compound of formula 8

Step 2 hydrogenating compound of formula 8 using catalytic hydrogenation process to obtain a compound of formula 9

Step 3 reacting a compound 9 with t-butyl magnesium halide in presence mixture of tetrahydrofuran and diethyl-ether to obtain a compound of formula 2c The compounds of formula 2, as used in step a above, is represented by a compound of formula 2b Formula 2b

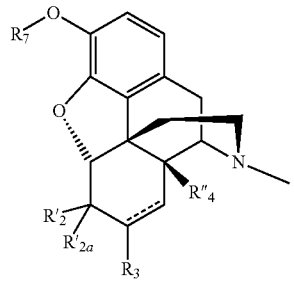

may be prepared by a process known in the art. The conventional process involves the reacting thebaine, under oxidizing conditions, with peroxide and a per acid to obtain an oxidized product possessing 6-oxo substitution and a beta oriented hydroxyl group at the 14-position, followed by hydrogenation of the oxidized product to obtain compounds with a fully saturated ring C and subsequent O-demethylation to obtain compound of the formula 10

Formula 10

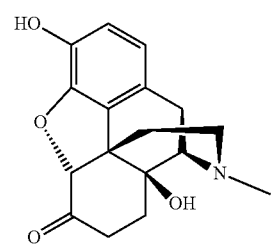

Starting with the compound of formula 10, a number of compounds of formula 2b may be prepared. For example the compound of formula 10 may be subjected to reduction using a metal hydride reagent to obtain compounds of formula 2b, wherein $R'_2$ is hydroxyl and $R'_{2a}$ is hydrogen as disclosed in British Patent No. 1119270, which is incorporated herein as a reference. Similarly compounds of formula 2b, wherein $R'_2$ and $R'_{2a}$ together represent =$CH_2$, may be prepared from compounds of formula 10, as disclosed in British Patent No. 1411129, which is incorporated herein as a reference. The compounds of formula 2b, wherein $R_2$ and $R_3$ together may form, together with the carbon atoms to which they are attached a group of the formula B Formula B

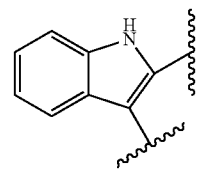

may be prepared from compounds of formula 10 by a process as disclosed in U.S. Pat. No. 4,816,586, which is incorporated herein as a reference.

The compounds of formula 10 which possess free hydroxy groups are susceptible to further reactions and thus needs to be suitably protected. The suitable hydroxy protecting groups may be, for example, acyl, benzyl, naphthylmethyl, t-butyl, silyl, preferably acyl, more preferably acetyl. This reaction may be carried out by a process well known in the art, for example, treatment with acetic anhydride, which may be carried out in absence of a solvent or in presence of a solvent, for example, in toluene, in anhydrous conditions.

In a preferred embodiment, the present invention relates to process of preparing compounds of formula I represented by buprenorphine, naltrexone, nalbuphine, naloxone, nalorphine, nalmefene, naltrindole, cyprenorphine, diprenorphine or semorphone. All the above named compounds are well known opiate drugs which are useful for treatment for treatment of one more of conditions selected from pain, drug addiction, drug overdose, alcoholism etc. in humans or veterinary animals.

In a still preferred embodiment of the present invention, the compound of formula 1 is represented by buprenorphine, represented by formula 1c Formula 1c

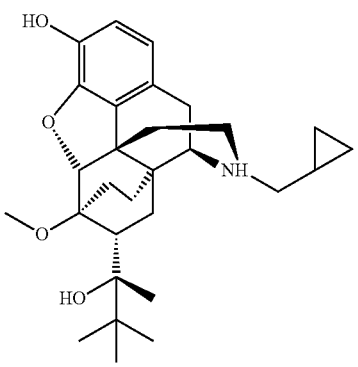

According to present invention, the process for preparation of buprenorphine comprises the steps of (a) reacting a compound of formula 2c Formula 2c

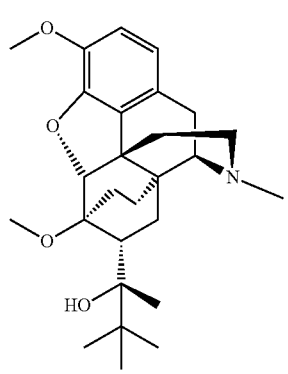

with ethylchloroformate in presence of an alkali iodide and Lithium carbonate to yield a compound of formula 3c:

Formula 3c

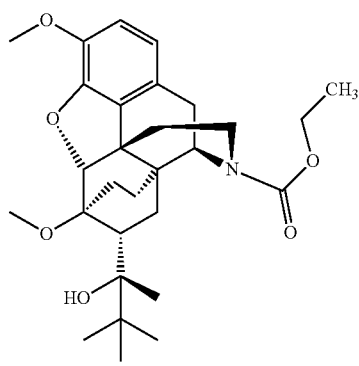

(b) subjecting the compound of formula 3c to hydrolysis in presence of potassium hydroxide to obtain a compound of formula 4c Formula 4c

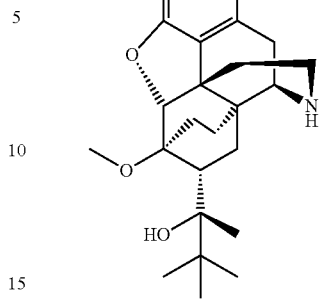

(c) reacting the compound of formula 4c with a compound of formula 5c, formula 5c

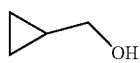

in presence of methanesulfonyl chloride and LiBr, to obtain a compound of formula 6c:

Formula 6c

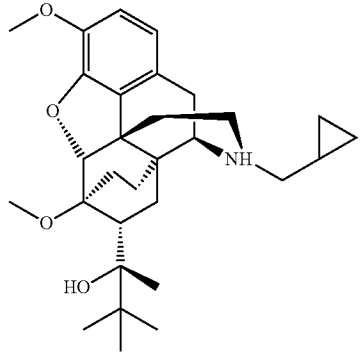

d) converting the compound of formula 6c to a compound of formula 1c or salt thereof by reacting with potassium tert-butoxide in presence of an $C_{1-4}$alkyl or arylthiol and optionally reacting with a mineral acid.

Some of the other morphinane derivatives namely cyprenorphine, diprenorphine may be prepared in a manner similar to buprenorphine.

In another preferred embodiment of the present invention, the compound of formula I is represented by naltrexone, represented by formula 1d Formula 1d

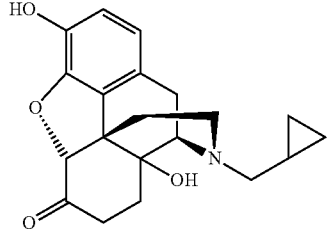

wherein the process comprises the steps of
(a) reacting a compound of formula 2d

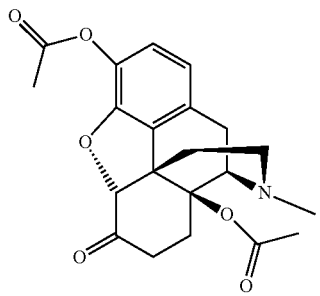

Formula 2d with ethylchloroformate in presence of an alkali iodide and lithium carbonate to obtain a compound of formula 3d;

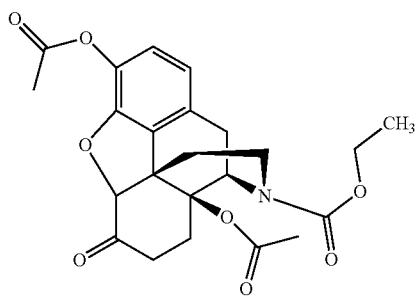

Formula 3d (b) subjecting the compound of formula 3d to hydrolysis in presence of an acid to obtain a compound of formula 4d

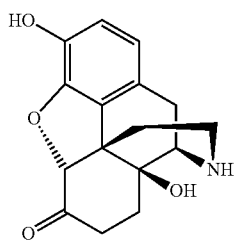

Formula 4d (c) reacting the compound of formula 4d with a compound of formula 5c

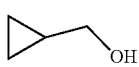

Formula 5c in presence of methane sulphonyl chloride and LiBr, to obtain a compound of formula 1d.
d) converting the compound of formula 1d to its salt.

The other morphinane derivatives namely nalbuphine, nalorphine, nalmefene, naltrindole, may be prepared in a manner similar to naltrexone.

In yet another preferred embodiment of the present invention, the compound of formula 1 is represented by Naloxone, represented by formula 1e

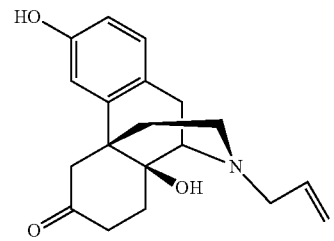

Formula 1e wherein the process comprises the steps of
(a) reacting a compound of formula 2d

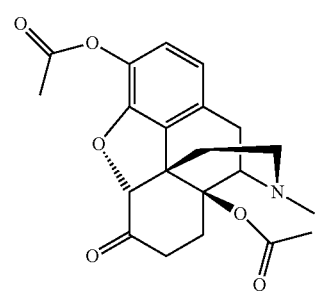

Formula 2d with ethylchloroformate in presence of an alkali iodide and lithium carbonate to obtain a compound of formula 3d:

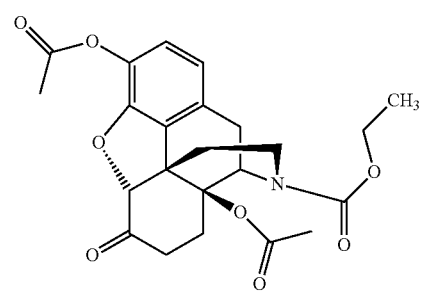

Formula 3d (b) subjecting the compound of formula 3d to hydrolysis in presence of an acid to obtain a compound of formula 4d

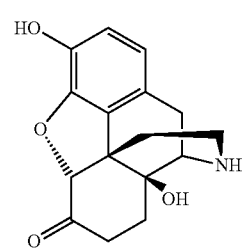

Formula 4d (c) reacting the compound of formula 4d with a compound of formula 5e

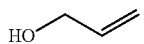

Formula 5e in presence of methane sulphonyl chloride and LiBr, to obtain a compound of formula 1e:

d) converting the compound of formula 1e to its salt.

The Following examples further illustrate the present invention. It should be understood however that the invention is not limited solely to the particular examples given below.

Example 1

Preparation of Buprenorphine

Step 1: Preparation of 7-Acetyl-6,14-endo-ethano-6,7,8,14-tetrahydrothebaine

Thebaine (20 Kg) was added to methyl vinylketone (22 L) at room temperature and the reaction mixture was heated at 80-90° C. for 3.0 hrs. After completion of the reaction, excess methyl vinylketone was distilled out under vacuum at a temperature below 60° C., further co-distilled with methanol (20 L×2) and finally the product was collected from the distillation flask by treatment with methanol (40 L) at 0-5° C., filtering and drying the residue obtained. Yield: 22.0 Kg Step 2: Preparation of 7-Acetyl-6,14-endoethano-6,7,8,14-tetrahydrothebaine 7-Acetyl-6,14-endoetheno-6,7,8,14-tetrahydrothebaine (18.5 Kg) (prepared in the step 1, example 1 above) was dissolved in 10% acetic acid solution (111 L) at 40-45° C., charcoalised and 5% Pd/C (1.387 Kg, 50% wet) was charged to it. Hydrogen gas was purged at 25-30° C. and the reaction was maintained at 25-30° C. for 5-6 hrs. After reaction completion, Pd/C was filtered out and the residue was washed with 10% acetic acid solution (37 L) and made alkaline (pH 9.0-10.0) using aqueous ammonia. The product was extracted with MDC (55.5 L×1, 18.5 L×1) and the combined organic layer was washed with DM Water (18.5 L×1). MDC was distilled out and the traces of MDC was co-distilled using methanol (18.5 L). The Product was leached by treatment with Methanol (55.5 L) and filtered Yield: 15.4 Kg Step 3: Preparation of 7α-(2-hydroxy-3,3-dimethyl-2-butyl)-6,14-endo-ethano-6,7,8,14-tetrahydrothebaine (a) Preparation of the t-butyl magnesium chloride Mg (3.8 Kg) was heated at 90-95° C. for 2.0 Hrs, Iodine (10.0 gm) and THF (14 L) was added to it. The reaction mixture was cooled to a temperature less than 40° C. and a lot of t-butylchloride (4.0 L) was added to it. The reaction mixture was stirred and a solution of t-butylchloride (24 L) in diethyl ether (180 L) was added to the reaction mixture over 4.0-5.0 hrs. The reaction mixture was maintained under stirring for 12-14 hrs at 25-30° C.

(b) 7-Acetyl-6,14-endo-ethano-6,7,8,14-tetrahydrothebaine (6.0 Kg) was added to t-butyl magnesium chloride in THF and ether as prepared in step (a) above, between 10-15° C. and stirred for 2.0 Hrs. The reaction mass was quenched in solution of ammonium chloride (40.2 Kg) in DM water (120 L) and the ether layer was separated. The aqueous layer was extracted with ether (90 L×2) and the combined organic layer was washed with DM water (120 L). The organic solvent was distilled out and product was isolated from the distillation flask by treatment with methanol, filtration and drying the residue obtained. Yield: 5.22 Kg Step 4: Preparation of 7α-(2-hydroxy-3,3-dimethyl-2-butyl)-6,14-endo-ethano-6,7,8,14-tetrahydronorthebaine (a) A Mixture of 7α-(2-hydroxy-3,3-dimethyl-2-butyl)-6,14-endo-ethano-6,7,8,14-tetrahydrothebaine (10 Kg), ethylchlorformate (58.3 L), sodium iodide (16.64 Kg) and lithium carbonate (5.0 Kg) in chlorobenzene (56 L) was heated at 95-105° C. for 14 hrs. After completion of the reaction, the reaction mixture was diluted with toluene (60 L). The inorganic solid was filtered out and washed with Toluene (60 L). ethylchloroformate, chlorobenzene and toluene was distilled out under vacuum and the residue degassed to give crude carbamate compound.

(b) Diethylene glycol (54 L) and Potassium hydroxide (31.4 Kg) were added to the degassed carbamate compound obtained in step (a0 above and heated at 130-140° C. for 3.0 hrs. After the completion of the reaction, the reaction mixture was cooled to below 30° C. and DM water (400 L) was added to it. The reaction vessel was further cooled to 0-5° C. and the solid product obtained was filtered, washed with DM water and dried. Yield: 9.02 Kg Step 5: Preparation of N-cyclopropylmethyl-7α-(2-hydroxy-3,3-dimethyl-2-butyl)-6,14-endo-ethano-6,7,8,14-tetrahydronorthebaine Methanesulphonyl chloride (5.31 L) was added to a mixture of cyclopropyl methanol (5.71 L) and triethylamine (20.13 L) in DMF (30.9 Ll) at a temperature of 0-5° C. The solution was maintained 3.0 hrs at 0-5° C. Lithium bromide (6.22 Kg) was added to the reaction mixture at 0-15° C. and maintained at this temperature for 3.0 hrs. 7α-(2-hydroxy-3,3-dimethyl-2-butyl)-6,14-endo-ethano-6,7,8,14-tetrahydronorthebaine (6.18 Kg) was added to above reaction mixture at 0-5° C. and the temperature was raised to 65-70° C. over a period of 1.0 hr. the reaction mixture was maintained at 65-70° C. for 14-15 hrs. After completion of the reaction, the reaction was quenched in DM Water (124 L) at a temperature below 20° C. The aqueous solution was basifies to a pH>9.0 and the product was extracted with toluene (62 L×1, 31 L×2) at more than 9.0 pH. The combined toluene layer was washed with DM water (31 L) followed by 10% Brine Solution (31 L) and concentrated to obtain the solid product which was isolated from the distillation flask by treatment with methanol (31 L), filtration and drying the residue obtained. Yield=5.84 Kg Step 6: Preparation of (2S)-2-[(−)-(5R,6R,7R,14S)-9α-cyclopropylmethyl-4,5-epoxy-6,14-ethano-3-hydroxy-6-methoxymorphinan-7-yl]-3,3-dimethylbutan-2-ol Potassium tert-butoxide (12 Kg) was added to the solution of thiophenol (9.45 L) in DMSO (22.2 L) over 1.0 to 3.0 hrs at a temperature below 20° C. N-cyclopropylmethyl-7α-(2-hydroxy-3,3-dimethyl-2-butyl)-6,14-endo-ethano-6,7,8,14-tetrahydronorthebaine (7.4 Kg) was added at RT to the solution of potassium ter-butooxide and thiophenol in DMSO and the reaction mixture was heated to a temperature of 126-132° C. the reaction was maintained at 126-132° C. for 6.0-8.0 hrs. After completion of the reaction, it was cooled to below 25° C. and diluted with DM water (222 L) followed by a solution of citric acid (37 Kg) in DM Water (37 L) to obtain pH below 3.5, further dilute H₂O₂ solution (~30%, 5 L) was added to it. The solution was washed with Toluene (74 L×3). Further the aqueous layer was basified with aqueous ammonia and extracted with ethyl acetate (74 L×3). The solvent was distilled out and product was isolated by Methanol (22 L) at 0-5° C. and dried. Yield=4.42 Kg Step 7—Preparation of Buprenorphine Hydrochloride Conc. HCl (2.6 L) was added to the filtered solution of buprenorphine base (9.65 Kg) in acetone (68 L) at below 15° C. to get pH below 2.0 and stirred for 1.0-2.0 hrs. The HCl salt firmed was filtered, washed with acetone and finally leached with filtered DM water (28 L) at 80° C. and dried. Yield=8.42 Kg.

Example 2

Preparation of Naltrexone

Step 1: Preparation of 4,5α-Epoxy-14-hydroxy-3-methoxy-17-methylmorphinan-6-one 50 kg thebaine was added to a solution of formic acid (145 kg) maintained at a temperature below 15° C. the solution was heated to 25° C. and maintained at this temperature for 1.0 hr. the reaction mixture was cooled to 0-5° C. and 30% $H_2O_2$ aqueous solution (5.5 kg 100% $H_2O_2$) was added at 0-5° C. The reaction mixture was maintained at 20-25° C. for 3.0 hrs. After completion of the reaction, it was quenched in 560 lit DM water and treated with charcoal. To the filtrate 5% Pd/C (1.5 kg) was added and hydrogen gas purged at 20-25° C. The reaction mixture was maintained at 20-25° C. for 4-5 hrs. After reaction completion, the catalyst was filtered off and the pH of the filtrate was adjusted to 9-9.5 with aqueous ammonia. The product was extracted with methylene dichloride and subsequently concentrated to obtain a solid which was isolated with IPA. Yield: 41.7 kg Step 2: Preparation of 4,5α-Epoxy-3,14-dihydroxy-17-methyl morphinan-6-one 30 kg of DL-Methionine was added to a solution of methane sulphonic acid (390 kg) maintained at 15-20° C. and stirred for 30 minutes. To this solution, 4,5α-Epoxy-14-hydroxy-3-methoxy-17-methylmorphinan-6-one (40 kg) was added at 20° C. and the reaction mass was heated to 50-55° C. the reaction mixture was maintained at 50-55° C. for 12.0 hrs. After reaction completion, it was quenched in a mixture of methanol (400 L) and water (800 L) and the pH of the resultant solution was adjusted to 9-9.2 with aqueous ammonia at below 20° C. The product was extracted with methylene dichloride and concentrated to obtain the product which was isolated with cyclohexane. Yield: 33.4 kg Step 3: preparation of 4,5α-Epoxy-3,14-dihydroxy morphinan-6-one (Noroxymorphone)

A mixture of 4,5α-Epoxy-3,14-dihydroxy-17-methyl morphinan-6-one (32.0 kg), toluene (225 L) and acetic acetic anhydride (32 L) were heated to 95-100° C. and maintained for 8.0 hrs. After reaction completion, the solvent was distilled at 60-65° C. under vacuum and acetic anhydride traces were stripped out with toluene and the residue degassed. Chlorobenzene (290 L), lithium carbonate (23.5 kg), sodium iodide (20.8 kg), DM water (3.2 L) and ethylchloroformate (280 L) were added to the degassed mass and heated to 95-105° C., the reaction was maintained at 95-105° C. for 12.0 hrs. After reaction completion, the solids were filtered and filtrate was concentrated at 70° C. under vacuum and the residue degassed. To the degassed mass acetic acid (96 L) and 15% aqueous sulphuric acid (480 L) was added and the solution was heated to 100-110° C. and maintained at 100-110° C. for 24 hrs. After reaction completion, the reaction mass was cooled to 0-5° C. and pH of the solution was adjusted to ~4.0 with aqueous ammonia. The aqueous solution was washed with MDC and the aqueous layer was separated. The separated aqueous layer was treated with activated charcoal and filtered. The pH of the filtrate was adjusted to 9-9.5 with aqueous ammonia at below 20° C., the solution was further cooled to 0-5° C. and the product formed was filtered and dried. Yield: 20.3 kg.

Step 3: Preparation of Naltrexone Base

Methanesulphonyl chloride (76 kg) was added to the mixture of cyclopropyl methanol (50 kg) and triethylamine (192 L) in DMF (400 L) maintained at 0-5° C., the reaction mixture was maintained at 0-5° C. for 3.0 hrs. Lithium bromide (60 Kg) was added to reaction mixture at 0-15° C. and maintained for 10-15 minutes. Noroxymorphone (40 Kg) was added to above reaction mixture at 0-5° C. and temperature raised to 65-70° C. over 1.0 hr period and maintained for 14-15 hrs. After completion of reaction it was quenched in ice-water below 20° C. and the product was extracted with ethylacetate, The ethylacetate layer was concentrated and the product was isolated with MDC and cyclohexane mixture at 10-15° C. Yield=35.3 Kg.

Step 4: Preparation of Naltrexone Hydrochloride 70 kg Naltrexone base is taken in 210 Lit DM water and pH was adjusted to ~2.0 with Conc.HCl and heated to 70-75° C. to get clear solution, filtered to make particle free and slowly cooled to 2-5° C. in 6-8 hrs period, filtered and then dried. The base was generated from filtrate by treatment with sodium hydroxide and converted to HCl salt by repeating the above mentioned process. Yield: 59.8 kg Comparative Examples Example 3

Preparation of (2S)-2-[17-(ethoxycarbonyl)-4,5α-epoxy-3,6-dimethoxy-6α,14-ethano-14α-morphinan-7α-yl]-3,3-dimethylbutan-2-ol without using Sodium iodide

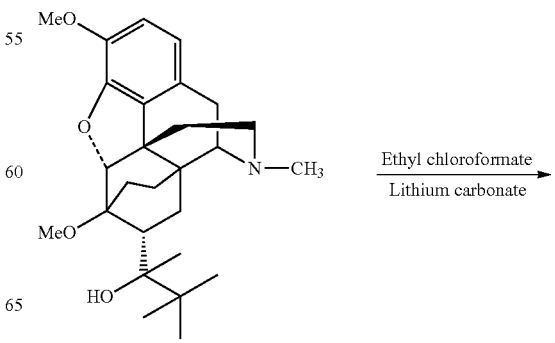

27

-continued

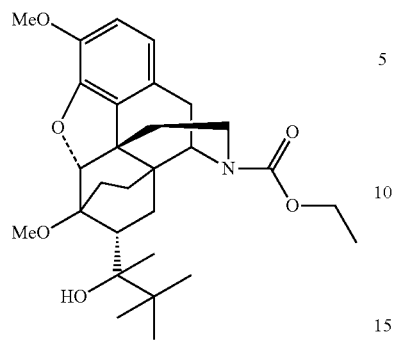

A mixture of 7α-(2-hydroxy-3,3-dimethyl-2-butyl)-6,14-endo-ethano-6,7,8,14-tetrahydrothebaine (5.0 g), ethylchloroformate (29.15 ml) and lithium carbonate (2.5 g) in chlorobenzene (28 L) was heated at 95-105° C. for 14 hrs. The reaction was monitored by TLC, only ~50% of reaction completion was observed.

Example 4

Preparation of 3,14-Diacetoxy-4,5α-epoxy-17-ethoxycarbonyl-morphinan-6-one without Using Sodium Iodide

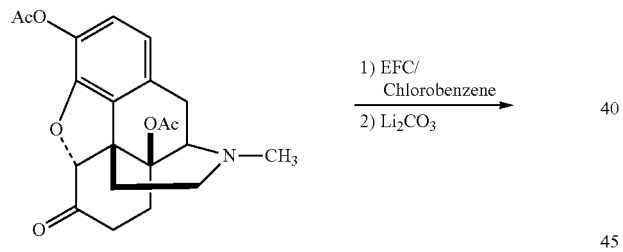

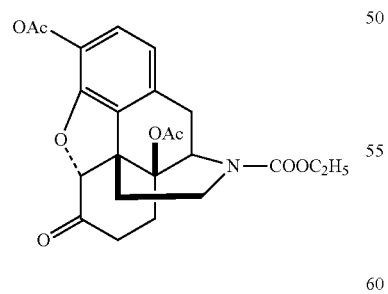

Mixture of 4,5α-Epoxy-3,14-diacetoxy-17-methyl morphinan-6-one (2.0 g), ethylchloroformate (13.71 ml), lithium carbonate (1.14 g) and DM Water (0.16 ml) in chlorobenzene (14.3 ml) was heated at 95-105° C. for 12 hrs. About ~50% of the reaction product was formed as found by TLC.

28

We claim:

1. A process for preparation of buprenorphine, represented by formula 1c

Formula 1c

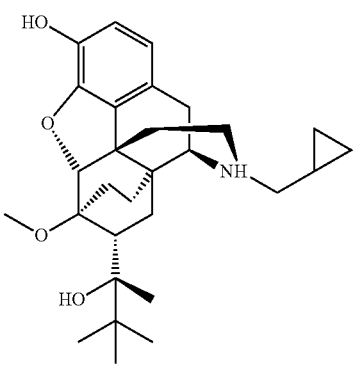

wherein the process comprises the steps of
(a) reacting a compound of formula 2c Formula 2c

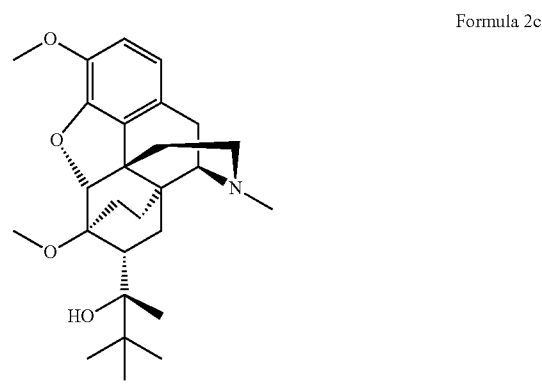

with ethylchloroformate in presence of an alkali iodide and Lithium carbonate to yield a compound of formula 3c:

Formula 3c

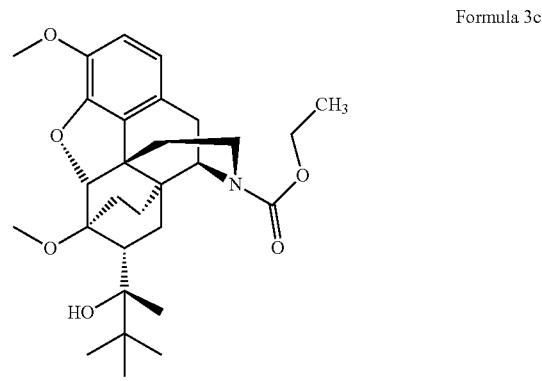

(b) subjecting the compound of formula 3c to hydrolysis in presence of potassium hydroxide to obtain a compound of formula 4c

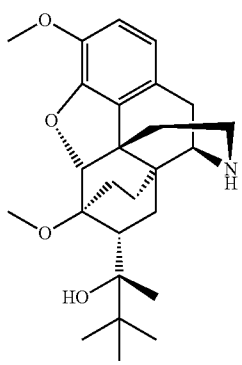

Formula 4c (c) reacting the compound of formula 4c with a compound of formula 5c

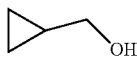

Formula 5c in presence of methanesulfonyl chloride and LiBr, to obtain a compound of formula 6c,

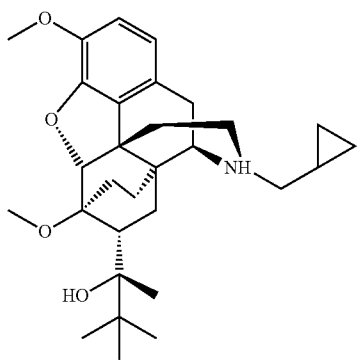

Formula 6c d) converting the compound of formula 6c to a compound of formula 1c or salt thereof by reacting with potassium tert-butoxide in presence of an $C_{1-4}$alkyl or an arylthiol and optionally reacting with a mineral acid.

2. The process as claimed in claim 1, wherein the alkali iodide is sodium iodide.

3. The process as claimed in claim 1, wherein the ethylchloroformate, lithium carbonate and alkali iodide are used in a ratio of 1:3:5.

4. The process as claimed in claim 1, wherein step d is carried out at a temperature below 200° C.

5. The process as claimed in claim 1, wherein the reaction is carried out at a temperature between 100-150° C.

6. The process according to claim 1, for preparing compound of formula 2c,

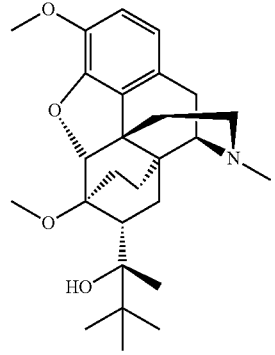

Formula 2c which comprises the steps of:
(a) reacting thebaine with methylvinyl ketone to form a compound of formula 8

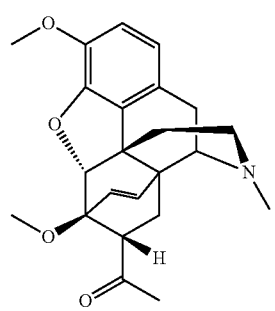

Formula 8

(b) hydrogenating the compound of formula 8 using catalytic hydrogenation process to obtain a compound of formula 9,

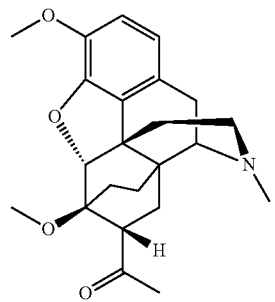

Formula 9

(c) reacting a compound of formula 9 with t-butylmagnesium chloride in presence mixture of tetrahydrofuran and diethylether to obtain a compound of formula 2c.

7. A process according to claim 6, wherein the concentration of tetrahydrofuran in ether is about 1-15%.

8. A process according to claim 6, wherein the concentration of tetrahydrofuran in ether is about 6-10%.

9. A process according to claim 6, wherein thebaine and methylvinylketone are used in a molar ratio of about 1:4.

10. A process as claimed in claim 6, wherein step a is carried out in absence of a solvent.

11. A process according to claim 6, wherein hydrogenation is carried out at atmospheric pressure.

12. A process according to claim 6, wherein hydrogenation is carried out in presence of acetic acid as solvent.

* * * * *